United States Patent [19]

Machlowitz et al.

[11] 4,096,035
[45] Jun. 20, 1978

[54] SEPARATION OF TRACHOMA AGENT FROM GROWTH MEDIUM IMPURITIES

[75] Inventors: Roy A. Machlowitz, Glenside; Edward H. Wasmuth, Telford, both of Pa.

[73] Assignee: Merck & Co., Inc., Rahway, N.J.

[21] Appl. No.: 806,651

[22] Filed: Jun. 15, 1977

[51] Int. Cl.² ............................................. C12K 7/00
[52] U.S. Cl. .................................................... 195/1.5
[58] Field of Search ........................................ 195/1.5

[56] References Cited

U.S. PATENT DOCUMENTS 4,024,243   5/1977   McAleer et al. .................... 195/1.5

OTHER PUBLICATIONS

Melnick et al. –Southern Medical J. vol. 69, No. 4, Apr. 1976, p. 469.
Wang et al. –Am. J. Opthal. vol. 63, No. 5, Part II, May 1967, pp. 1443–1453.

*Primary Examiner*—Sam Rosen
*Attorney, Agent, or Firm*—Donald J. Perrella

[57] ABSTRACT

Trachoma agent is separated from growth medium impurities by density gradient centrifugation in a sodium bromide solution.

8 Claims, No Drawings

SEPARATION OF TRACHOMA AGENT FROM GROWTH MEDIUM IMPURITIES

BACKGROUND OF THE INVENTION

Trachoma agent is a chlamydia which causes a chronic contagious conjunctivitis marked by inflammatory granulations on the conjunctival surfaces. Trachoma agent can be grown in eggs or in tissue culture, but the harvested trachoma agent is in suspension with extraneous protein and cellular debris from the eggs or from the tissue culture.

OBJECTS OF THE INVENTION

It is an object of the present invention to provide a method for separating trachoma agent from growth medium impurities. Another object is to provide a method for separating trachoma agent from the extraneous protein and cellular debris harvested with it. These and other objects of the present invention will be apparent from the following description.

SUMMARY OF THE INVENTION

Trachoma agent is separated from extraneous protein and debris collected with the harvested trachoma agent by density gradient centrifugation in a sodium bromide solution.

DETAILED DESCRIPTION

The present invention is based on the finding that trachoma agent may be separated from extraneous protein and cellular debris by density gradient centrifugation in a sodium bromide solution.

The trachoma agent may be grown in conventional fashion by inoculating eggs or tissue culture with live infectious trachoma agent. The infection is then allowed to progress to the point wherein the titer of trachoma agent is at about its maximum. The growth medium, the yolk sac in the case of eggs, is then comminuted in a diluent containing sucrose and phosphate buffer, and preferably inactivated with formaldehyde. In the case of tissue culture, the cells are dispersed into the tissue culture fluid and comminuted. The resulting suspension in either case is centrifuged at low speed. Where the growth medium is eggs, the middle layer is selected from NaBr treatment, and where the growth medium is tissue culture, the supernatant layer is selected for NaBr treatment.

The sodium bromide is employed in the form of a gradient containing from about 15% to about 40% NaBr. (All NaBr solutions are % wt/wt). Preferably the gradient is in the form of a step gradient containing the following density regions: 20% NaBr, 27.5% NaBr and 35% NaBr. The trachoma agent is centrifuged through the NaBr gradient at a speed of from about 20,000 to about 300,000 X g for from about 1 hour to about 5 hours, or until the trachoma agent is in the density region of from about 1.25 g/ml to about 1.30 g/ml.

The sodium bromide may be removed from the trachoma agent-rich fractions by centrifugation, dialysis or chromatographic separation using conventional techniques. The trachoma agent may be obtained from the foregoing treatment in a physiologically acceptable medium, or may be reconstituted in such medium. Phosphate buffered saline (PBS) is an example of a preferred dialysis or reconstituting medium.

The purified trachoma agent of the present invention is a useful starting material for preparing a vaccine against trachoma agent.

The following examples illustrate the present invention without, however, limiting the same thereto.

EXAMPLE 1

Starting material

Yolk Sac dispersion 150 embryonated chicken eggs are innoculated with Trachoma seed material. These eggs are harvested after about 7 days. About two grams of yolk sac are recovered from each usable egg. As about 50% of the eggs are usable at harvest, about 150 gms of yolk sac are obtained from this batch. The 150 gms of yolk sac is diluted with 150 ml of 4SP, i.e., 17% sucrose in (PBS).

Step 1:

Low speed clarification of yolk sac dispersion (to remove fat and debris).

The starting material (300 ml) is centrifuged in a refrigerated low-speed centrifuge (type PR-2 manufactured by International Equipment Co.) (IEC), at 400 X g for 10 minutes. The fluid is decanted through two layers of sterile cheesecloth. About 270 ml of fluid is recovered.

Step 2:

High Speed clarification and concentration (Optional)

The material from step 1 is centrifuged at 20,000 X g (15,000 RPM) for 1 hour in a fixed angle rotor (type 30 manufactured by Spinco Div., Beckman Instruments Inc.). The supernatant fluid and fat are decanted and discarded. The fat which adheres to the upper part of the bottle is removed with a rubber policeman. The pelleted material is dispersed and resuspended to about 40% of the starting fluid volume (108 ml) in PBS. The suspension is stirred to obtain a more homogeneous dispersion.

Step 3:

Density gradient centrifugation

A line of six 20 ml syringes with plunger removed and a 20G X 1.5 inch (3.8 cm) needle attached are clamped above six 1 X 3 ½ inch (2.5 X 8.9 cm) Beckman SW 27 cellulose nitrate tubes so that a needle point rests on the top of the inside wall of each tube. Eight and one-half ml of 35% NaBr is pipetted into each cellulose nitrate tube. Seventeen ml of 27.5% NaBr is pipetted into each syringe and allowed to run into the cellulose nitrate tubes. Eight and one-half ml of 20% NaBr is pipeted into each syringe and allowed to run into the tubes. Five ml of trachoma suspension is pipetted atop each gradient. The tubes are placed in a swinging bucket rotor (type SW 27 manufactured by Spinco Div., Beckman Instruments Inc.), and centrifuged at 26,000 rpm for 2 hours (290,000 X g average).

The bottom of each tube is punctured with a 25 gauge needle. The first six ml are collected and discarded. The next six ml are collected as the trachoma-rich fraction. The trachoma-rich fractions are recovered from each tube and pooled. The resulting 36 ml pool is diluted to 60 ml with PBS. The trachoma is pelleted in a Beckman Type 30 rotor at 20,000 RPM (36,000 X g) for 1 hour. The pellet is resuspended in 10 ml PBS.

EXAMPLE 2

Starting material:

500 Chicken eggs are harvested as in Example 1 yielding 500 gms of yolk sac fluid. This is diluted to 1000 ml with 4SP.

Step 1:

Low speed clarification of yolk sac dispersion.

The starting material (1000 ml) is centrifuged in the type PR-2 centrifuge at 400 X g for 10 minutes. The supernatant fluid is decanted through two layers of sterile cheesecloth. About 875 ml of fluid is recovered.

Step 2:

High speed clarification and concentration (Optional)

The material from step 2 is centrifuged at 20,000 X g for 1 hour in the type 19 rotor. The supernatant fluid and fat are decanted and discarded. The fat which adheres to the upper part of the bottle is removed with a ruber policeman. The pelleted material is dispersed and resuspended to about 40% of the starting fluid volume (about 350 ml). The suspension is stirred to obtain a more homogeneous dispersion.

Step 3:

Density gradient centrifugation.

A gradient consisting of 350 ml of 20% NaBr, 700 ml of 27.7% NaBr, and 625 ml of 35% NaBr is pumped at 50–70 ml/minute through the edge line into a batch rotor (type Ti-15 manufactured by Spinco Div., Beckman Instruments Inc.), which is spinning at 3,000 rpm. Trachoma suspension, 250 ml, followed by 25 ml of PBS are pumped through the core-line into the rotor forcing 275 ml of 35% NaBr out the edge line. The rotor is then accelerated to 35,000 rpm. After two hours the rotor is decelerated to 3,000 rpm. PBS is pumped into the rotor through the core line, pushing the gradient-trachoma mixture out the edge-line. The fractions are taken as follows: cut 1, 300 ml., is discarded, and fractions 2–6, 100 ml each, are saved as the trachoma rich material. The rest of the rotor volume is discarded. The trachoma rich cut, 500 ml, from fractions 2–6 in the 1.25 to 1.30 gm/ml density range at 20° C is removed for step 4.

Step 4:

Salt removal and trachoma concentration.

The trachoma rich cut, 500 ml, is diluted to 1500 ml with PBS and centrifuged in the type 19 rotor at 18,000 rpm (35,000 X g) for 90 minutes. The fluid is decanted and discarded. The trachoma pellet is resuspended in 30–50 ml PBS with 50 mcg/ml of thimerosal and 20 mcg/ml of formaldehyde.

EXAMPLE 3

Starting material:

Yolk sac dispersion - 1000 chicken eggs are harvested as in Example 1 yielding 2000 ml of yolk sac in 4SP.

Step 1:

Low speed clarification of yolk sac dispersion.

The starting material, 2000 ml is centrifuged in the type PR-2 centrifuge at 400 X g for 10 minutes. The supernatant fluid is decanted through two layers of sterile cheesecloth. About 1750 ml of fluid is recovered.

Step 2:

Density gradient centrifugation.

One thousand (1000) ml of fluid from Step 1 is pumped through the lower opening into the K-5 rotor. One thousand four hundred fifty (1450) ml of 20% NaBr, 2800 ml of 27.5% NaBr and 1450 ml of 35% NaBr are pumped through the lower opening into a batch rotor (type K-5 manufactured by Electro-Nucleonics Inc.) (ENI), at a rate of 100 ml/minute. The rotor accelerated to 35,000 rpm. After three hours at 35,000 rpm the rotor is stopped. The trachoma-gradient mixture is pumped out the lower line. The following cuts are taken: Cut 1, 750 ml, is discarded, and Cut 2, 2250 ml, is saved as the trachoma-rich fraction. Cut 3, the remaining volume is discarded. The trachoma rich cut has a density range 1.25 - 1.30 gm/ml at 20° C.

Step 3:

Salt removal and trachoma concentration.

(Same as step 4 in Example 2 except the trachoma fraction (2250 ml) is diluted to 4000 ml with PBS. the pellet from the Type 19 pelleting is resuspended to 60 ml with PBS.

EXAMPLE 4

Starting material:

5000 Chicken eggs are harvested as in Example 1. This yields 10,000 ml of yolk sac in 4SP.

Step 1:

Low speed clarification of yolk sac dispersion.

The starting material is centrifuged in the PR-2 at 400 X g for 10 minutes. The supernatant fluid is decanted through two layers of sterile cheesecloth. About 8,750 ml of fluid is recovered and diluted 3 fold with PBS.

Step 2:

Density gradient centrifugation.

A zonal rotor (type K-10) (ENI), is filled with 8400 ml of PBS at 1°–4° C. One thousand two hundred fifty (1250) ml of 20% NaBr followed by 2500 ml of 27.5% NaBr followed by 1250 ml of 35% NaBr (all at 1°–4′ C) are pumped through the lower opening into the rotor. The rotor is accelerated. At a speed of 5,000 rpm, trachoma suspension (1°–4° C) from Step 1 is pumped through the lower opening into the rotor at a flow rate of 100 ml/minute. Effluent fluid is forced out the top line and is discarded. The rotor continues to accelerate to 35,000 rpm. The trachoma flow rate is increased to 300 ml/minute. When all the trachoma fluid has passed through the rotor the rotor is stopped.

Step 3:

The trachoma rich cut (density range 1.25 - 1.30 gm/ml at 20° C) is recovered as in Step 2 of Example 3.

Step 4:

Salt removal and trachoma concentration.

(Same as Step 4 in Example 2 except the resuspension volume may be increased to 500 ml.)

What is claimed is:

1. A method of separating trachoma agent from impurities derived from the medium in which the trachoma agent has been grown which comprises subjecting the trachoma agent to isopycnic banding in a NaBr density gradient, and recovering fractions rich in trachoma agent.

2. A method according to claim 1 wherein the gradient is a step gradient.

3. A method according to claim 1 wherein the banding is continued until the trachoma agent is in the density region of from about 1.25 gm/ml to about 1.30 gm/ml.

4. A method according to claim 1 wherein the trachoma agent is recovered from the trachoma-rich fractions by centrifugation.

5. A method according to claim 1 wherein the trachoma agent is recovered from the trachoma-rich fractions by dialysis.

6. A method according to claim 1 wherein the trachoma agent is recovered from the trachoma-rich fractions by chromatographic separation.

7. A composition comprising trachoma agent in a liquid medium comprising NaBr.

8. A composition according to claim 7 having a density of from about 1.25 to about 1.30 gm/ml.

* * * * *